United States Patent
Cai (10) Patent No.: US 10,154,832 B2
(45) Date of Patent: Dec. 18, 2018

(54) SEMEN COLLECTION DEVICE

(71) Applicant: Danzhi Cai, Shenzhen (CN)

(72) Inventor: Danzhi Cai, Shenzhen (CN)

(73) Assignee: Danzhi Cai, Shenzhen (CN)

( * ) Notice: Subject to any disclaimer, the term of this patent is extended or adjusted under 35 U.S.C. 154(b) by 1011 days.

(21) Appl. No.: 14/547,798

(22) Filed: Nov. 19, 2014

(65) Prior Publication Data

US 2016/0135792 A1 May 19, 2016

(51) Int. Cl.
*A61B 10/00* (2006.01)
*A61H 19/00* (2006.01)
*A61H 23/02* (2006.01)
*A61F 5/453* (2006.01)

(52) U.S. Cl.
CPC .......... *A61B 10/0058* (2013.01); *A61F 5/453* (2013.01); *A61H 19/32* (2013.01); *A61H 23/0254* (2013.01); *A61H 2201/5058* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,316,895 A | * | 5/1967 | Lewis | A61B 10/0058 600/582 |
| 7,993,315 B2 | * | 8/2011 | Matsuura | A61B 10/0058 600/38 |
| 8,475,422 B2 | * | 7/2013 | Wu | A61B 10/0058 604/349 |
| 9,724,263 B2 | * | 8/2017 | Cai | A61H 19/32 |
| 2007/0049792 A1 | * | 3/2007 | Levy | A61H 19/44 600/38 |
| 2007/0112284 A1 | * | 5/2007 | Hoffman | A61B 5/0002 600/591 |
| 2008/0065187 A1 | * | 3/2008 | Squicciarini | A61F 2/26 607/143 |
| 2009/0171144 A1 | * | 7/2009 | Squicciarini | A61F 2/26 600/38 |
| 2010/0041944 A1 | * | 2/2010 | Levy | A61F 5/41 600/38 |
| 2010/0174257 A1 | * | 7/2010 | Matsuura | A61B 10/0058 604/347 |
| 2011/0098613 A1 | * | 4/2011 | Thomas | A61C 17/221 601/46 |
| 2012/0136289 A1 | * | 5/2012 | McGann | A61H 23/0263 601/78 |

(Continued)

*Primary Examiner* — Tatyana Zalukaeva
*Assistant Examiner* — Guy K Townsend
(74) *Attorney, Agent, or Firm* — ScienBiziP, P.C.

(57) ABSTRACT

A semen collection device includes a core member, a mounting unit, and a position sensing module. The core member defines an insertion space having an inlet at an end. The mounting unit includes a main body having a main portion and a receiving portion extending from an end of the main portion, a cover detachably installed on the receiving portion. The cover and the receiving portion cooperatively define a cylindrical chamber for fixedly receiving the core member, and further define an opening communicating with the chamber for exposing the end of core member having the inlet. The position sensing module is located in the main portion substantially close to the opening and configured to detect a variation of amplitude and frequency of a position of the core member.

16 Claims, 7 Drawing Sheets

(56) References Cited

U.S. PATENT DOCUMENTS

| | | | | |
|---|---|---|---|---|
| 2012/0215141 A1* | 8/2012 | Peddicord | ............... | A61H 19/00 601/46 |
| 2014/0018713 A1* | 1/2014 | Elenga | ............... | A61H 23/0218 601/78 |
| 2014/0046127 A1* | 2/2014 | Topolovac | ............... | A61H 19/44 600/38 |
| 2014/0336452 A1* | 11/2014 | Shahoian | ............... | A61H 19/30 600/38 |
| 2015/0119770 A1* | 4/2015 | Driscoll | ............... | A61H 23/02 601/48 |
| 2016/0135792 A1* | 5/2016 | Cai | ............... | A61B 10/0058 601/46 |
| 2016/0136034 A1* | 5/2016 | Cai | ............... | A61H 19/32 600/38 |
| 2016/0136036 A1* | 5/2016 | Cai | ............... | A61H 19/34 601/46 |
| 2016/0136038 A1* | 5/2016 | Cai | ............... | A61H 19/44 601/46 |
| 2017/0258456 A1* | 9/2017 | Wu | ............... | A61H 19/00 |

* cited by examiner

SEMEN COLLECTION DEVICE

CROSS-REFERENCE TO RELATED APPLICATIONS

This application is related to two co-pending U.S. patent application Ser. Nos. 14/547,785, 29/509,611), entitled "CORE MEMBER FOR SEMEN COLLECTION DEVICE", "SEMEN COLLECTION DEVICE", by Danzhi Cai. The applications have the same assignee as the instant application and are concurrently filed on the same day. The disclosure of the above-identified applications is incorporated herein by reference.

FIELD

The subject matter herein generally relates to a semen collection device, and more particularly to an improvement of a semen collection device which has been conventionally used based on requirements for medical research and treatment and on social requirement for prevention of sex crime, prostitution, and spreading of sexually-transmitted disease, and the like.

BACKGROUND

There are proposed various semen collection devices for obtaining semen from a human male from a necessity of a medical research and a treatment. Semen collection devices are used for medical necessity, for example, examining a husband's sexual function from semen collected to investigate a cause of conjugal infertility, treating sexual dysfunction, and securing semen for artificial insemination. There is conventionally known a simple semen collection device which can be obtained at a low cost and does not cause a hygienic and health problems because it is a disposable type to satisfy various social needs such as prevention of a sexual crime, a prostitution, a decrease in the number of sexually-transmitted disease infected patients, and the like by solving a personal sexual desire.

BRIEF DESCRIPTION OF THE DRAWINGS

Many aspects of the present disclosure are better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising," when utilized, means "including, but not necessarily limited to"; it specifically indicates open-ended inclusion or membership in the so-described combination, group, series and the like.

Figure 1:
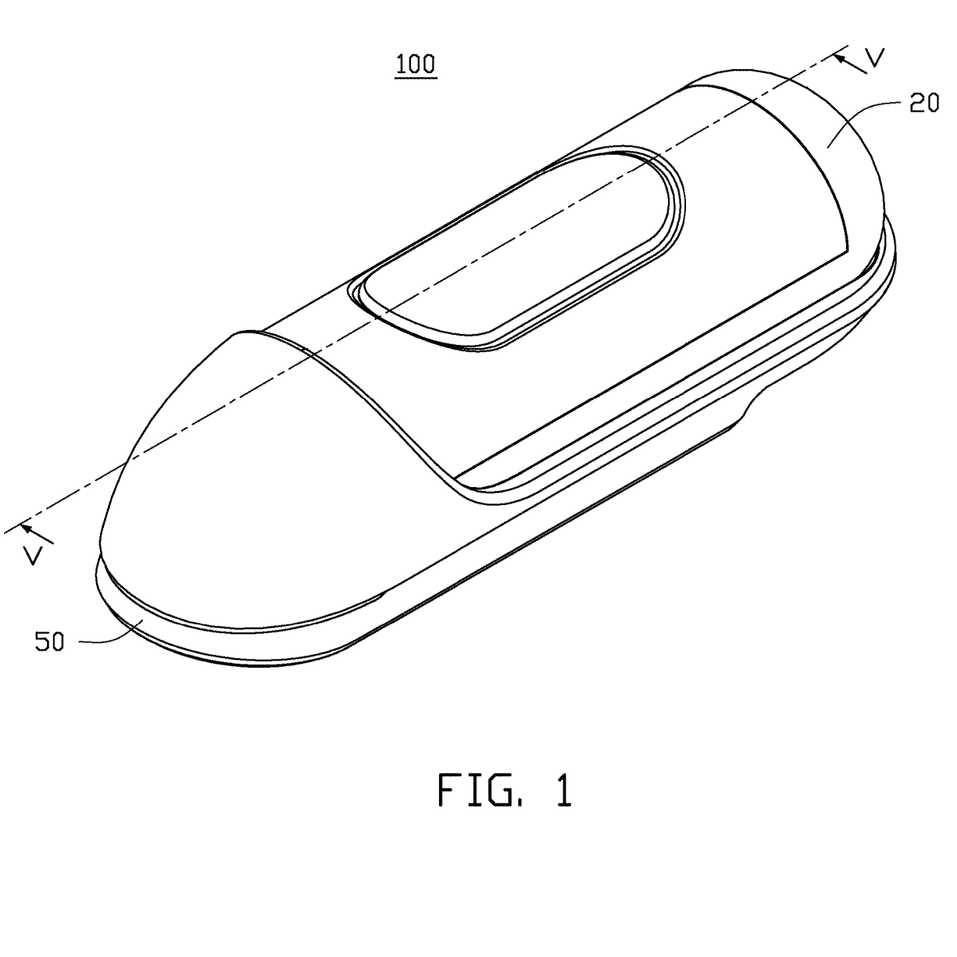
FIG. 1 is an isometric view of a first embodiment of a semen collection device including a core member, a mounting unit, and a base.
Figure 2:
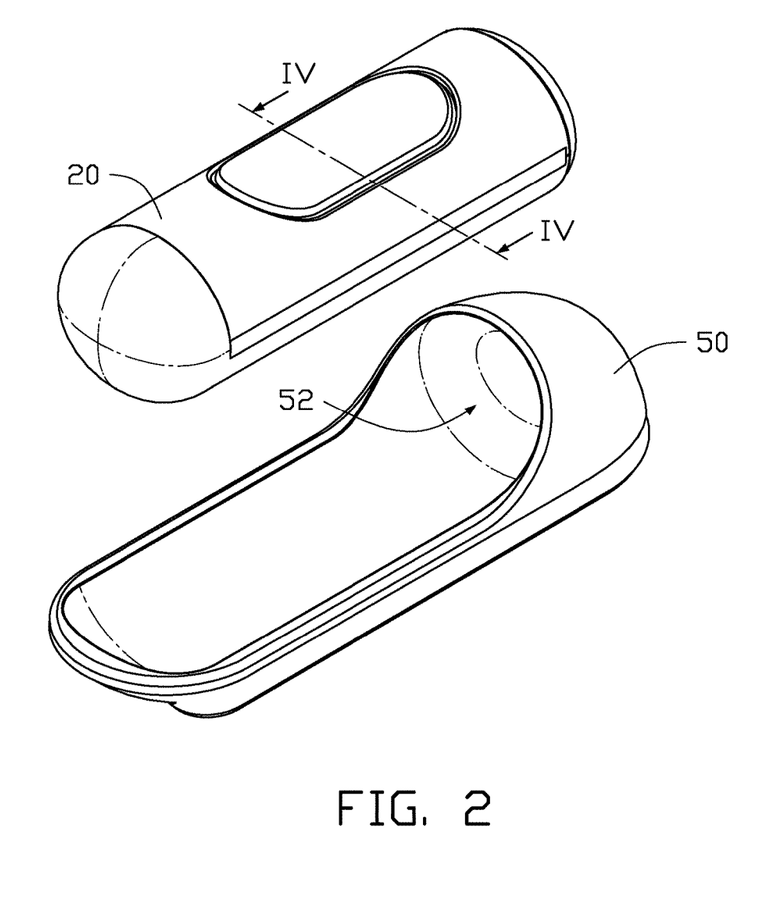
FIG. 2 is a partially exploded view of the semen collection device shown in FIG. 1.
Figure 3:
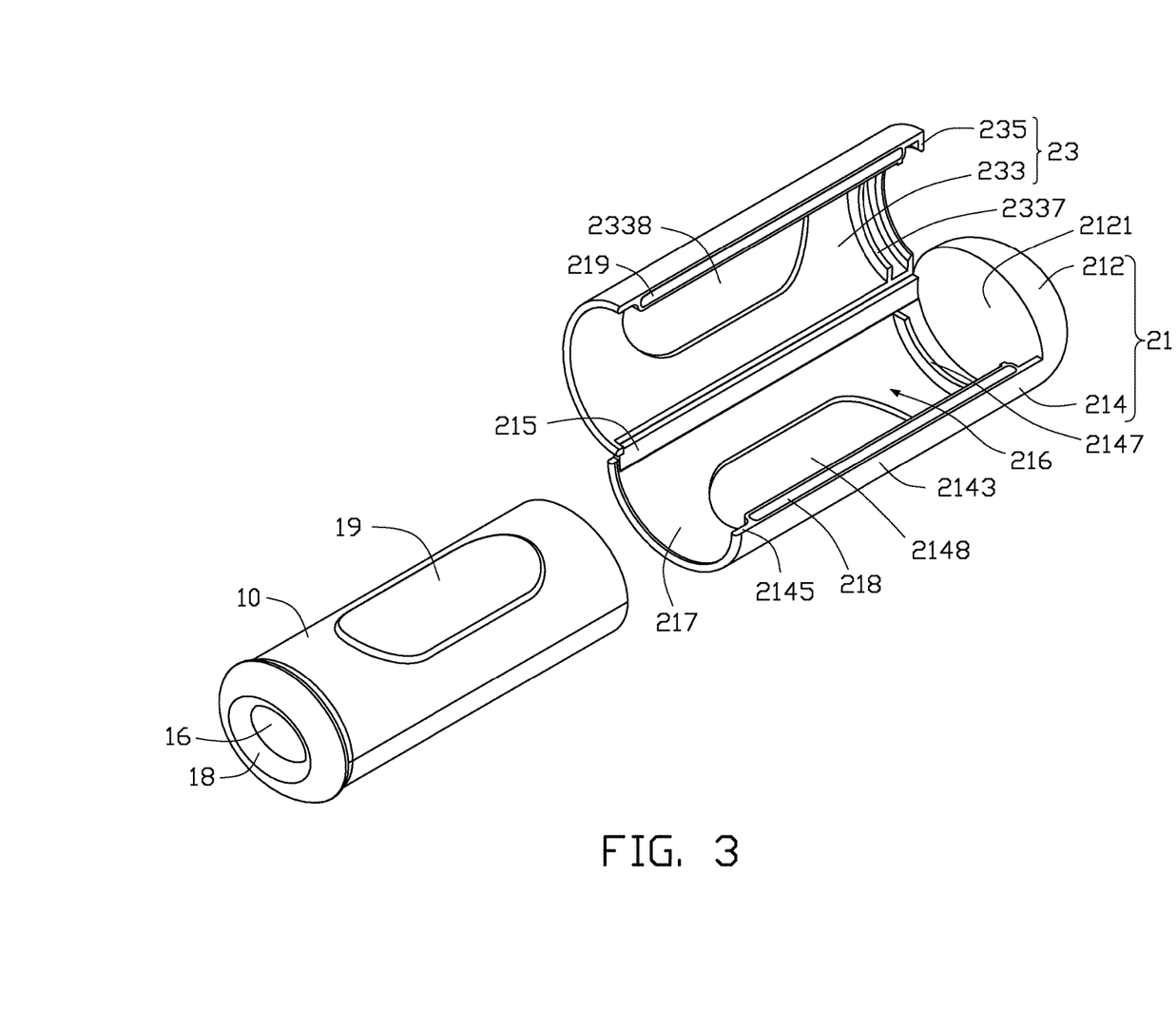
FIG. 3 is a partially exploded view of the core member and the mounting unit of the semen collection device shown in FIG. 1.

FIGS. 1-3 show a first embodiment of a semen collection device 100. The semen collection device 100 can include a core member 10, a mounting unit 20, and a position sensing module 25 (see FIG. 5), and a base 50. The core member 10 can define an insertion space 16 having an inlet 18 at an end. The mounting unit 20 can include a main body 21 and a cover 23. The main body 21 can include a main portion 212 and a receiving portion 214 extending from an end of the main portion 212. The cover 23 can be hingedly couple to the receiving portion 214 in an axial direction of the receiving portion 214 at a side of the main portion 212. The cover 23 can be opened or closed together with the receiving portion 214 of the main body 21. The cover 23 and the receiving portion 214 can cooperatively define a cylindrical chamber 216 for fixedly receiving the core member 10, and an opening 217 communicating with the cylindrical chamber 216 for exposing the end of core member 10 having the inlet 18. The position sensing module 25 is located in the main portion 212 substantially close to the opening 217 and configured to detect a variation of amplitude and frequency of a position of the core member 10. The base 50 can define a depression 52 to hold the mounting unit 20 with the core member 10.

The core member 10 can be a cylindrical structure including a flexible body 11 and a built-in piece 14. The flexible body 11 can include a flexible base 110 and an annular sidewall 114 extending from the flexible base 110 to form the cylindrical structure. The flexible body 11 can define the insertion space 16 having the inlet 18 at the end. The flexible body 11 can define a deformable surface 1102 at an outer surface of the flexible base 110 facing the main portion 212 of the mounting unit 20. The flexible body 11 can be composed of a soft resin such as gel-like resin and the like. The built-in piece 14 can be disposed in the annular sidewall 114 of the flexible body 11. The built-in piece 14 can be a tubular structure disposed in the annular sidewall 114 of the flexible body 11 and surrounding the insertion space 16. The built-in piece 14 can be composed of a material harder than the flexible body, such as a hard resin material. The built-in piece 14 can further defined a plurality of through holes (not labeled) and the flexible base 110 of the flexible body 11 can fill up the through holes. The flexible base 110 of the core member 10 comprised of a material more flexible than a material constituting the mounting unit or the built-in piece 14.

As shown in FIGS. 2 and 3, the main body 21 of the mounting unit 20 can define a substantially circular mounting surface 2121 at a side. The receiving portion 214 can include a first semi-cylindrical sidewall 2143 extending from a part of an edge of the circular mounting surface 2121. The mounting surface 2121 and the first and second semi-cylindrical sidewalls 2143, 235 cooperatively define the cylindrical chamber 216 for fixedly receiving the core member 10. The receiving portion 214 includes a pair of first end side surfaces 2145 extending along the axial direction of the receiving portion 214 substantially perpendicular to the circular mounting surface 2121. The cover 23 can include a second semi-cylindrical sidewall 233 having a pair of second end side surfaces 235 extending along the axial direction of the receiving portion 214 substantially perpendicular to the circular mounting surface 2121. One of the second end side surfaces 235 of the cover 23 is hinged with one of the first end side surfaces 2145 with a hinge 215.

The other of the first end side surfaces 2145 can define a first depression 2146 for fixing a first magnetic member 218, and the other of the second end side surface 235 can define a second depression 236 for fixing a second magnetic member 219 according to the first magnetic member 218. The cover 23 can be rotated relative to the receiving portion 213 until the second magnetic member 219 is adsorbed on the first magnetic member 218, thereby the cover 23 configured to closed on the receiving portion 213.

The first semi-cylindrical sidewall 2143 can further includes a first curved rib 2147 protruding out from an inner surface of the first semi-cylindrical sidewall 2143 adjacent to the circular mounting surface 2121 of the main portion 212. The second semi-cylindrical sidewall 233 can further includes a second curved rib 2337 protruding out from an inner surface of the second semi-cylindrical sidewall 233 adjacent to of the main portion 212 for matching with the first curved rib 2147, such that the first curved rib 2147 and the second curved rib 2337 cooperatively form a ring for limiting the end of the core member 10.

The first semi-cylindrical sidewall 2143 can further define a first through hole 2148 in the first semi-cylindrical sidewall 2143. The second semi-cylindrical sidewall 233 also can further define a second through hole 2338 in the second semi-cylindrical sidewall 233. The core member 10 can further include a pair of positioning plate 15 formed on the sidewall 114 according to the first and second through holes 2148, 2338, and exposed out of the first and second through holes 2148, 2338 correspondingly.

Figure 5:
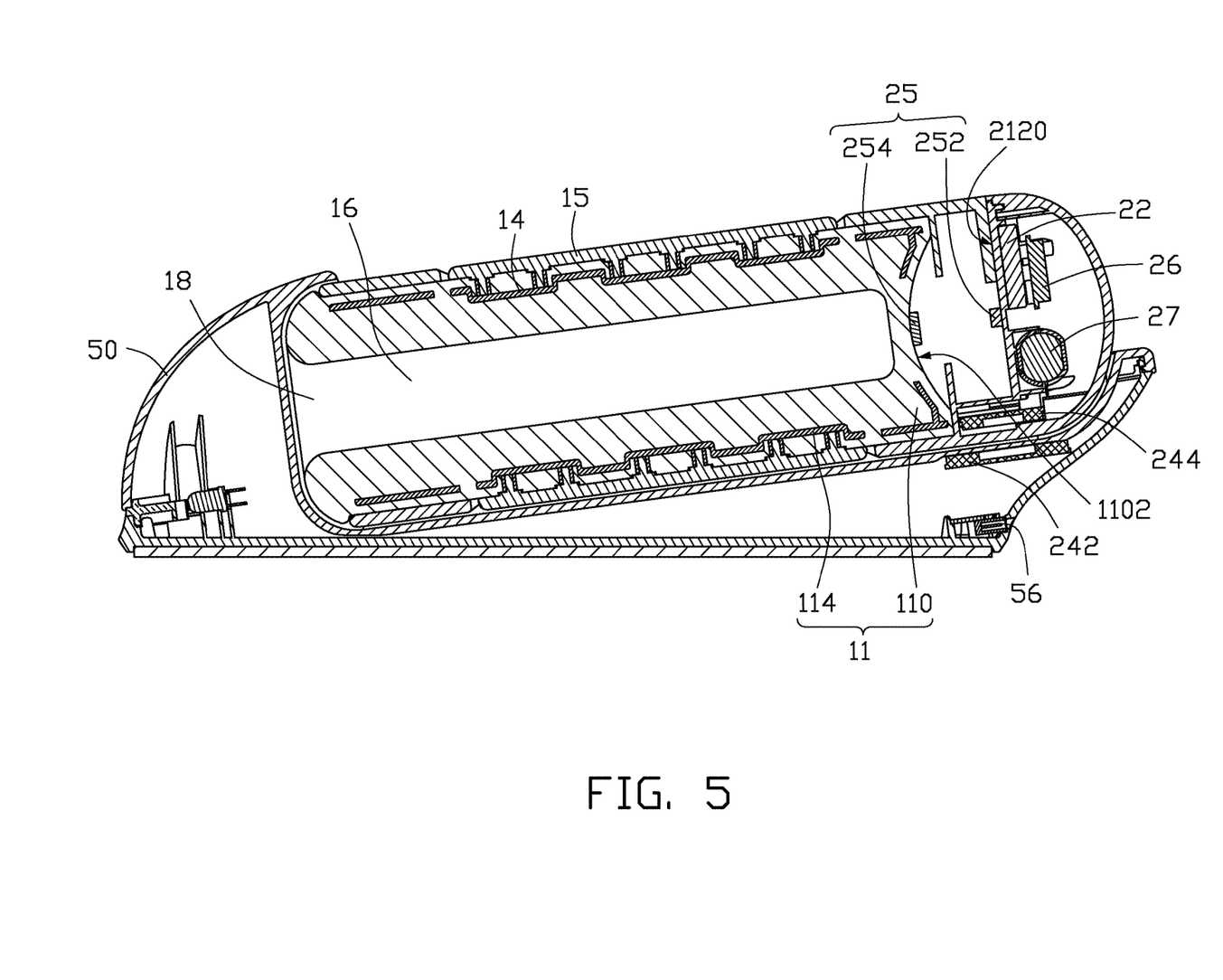
FIG. 5 is a cross-sectional view of the semen collection device shown in FIG. 1, taken along line V-V.

Referring to FIG. 5, the position sensing module 25 can include an infrared ray sensor 252 positioned in the main portion 212 toward the opening 18, and a light reflecting layer 254 formed at the deformable surface 1102 of the flexible base 110 of the flexible body 11 corresponding to the infrared ray sensor 252. The infrared ray sensor 252 can detect a changed of infrared ray reflected by the light reflecting layer 254 for detecting a variation of amplitude and frequency of a position of the core member during a penis moving in the insertion space 16.

The main portion 212 of the main body 21 can define a receiving chamber 2120. The main portion 212 of the main body 21 can further include a control circuit 22, a wireless communication module 29, a wireless charging module 24, a battery 26, and a vibratory element 27. The control circuit 22, the wireless communication module 29, the wireless charging module 24, the battery 26, and the vibratory element 27 are received in the receiving chamber 2120 of the main portion 212. The wireless communication module 29, the wireless charging module 24, the battery 26, the vibratory element 27, and the infrared ray sensor 252 of the position sensing module 25 electrically couple to the control circuit 22 respectively. The wireless communication module 29 is capable of receiving a control signal and transmitting to the control circuit 22 to control the vibration of the vibratory element 27.

In the illustrated embodiment, the vibratory element 27 can be positioned in the receiving chamber 2120 adjacent to the flexible base 110 of the core member 10. The vibratory element 27, such as motors, can be controlled to affect the actuation or vibration of one or more portions of the semen collection device 100. The vibratory element 27 can be configured to provide contrasting, overlapping, and/or cumulative vibratory behavior in the semen collection device 100 that affects the entire body of the semen collection device 100.

Figure 4:
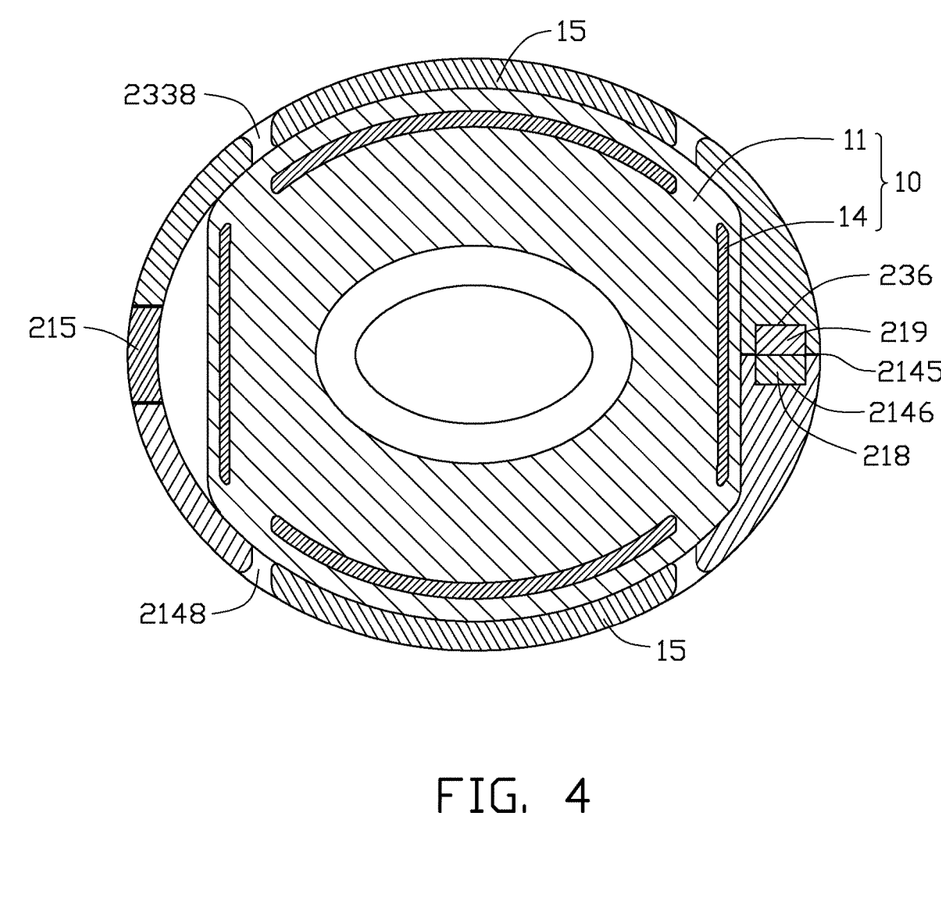
FIG. 4 is a cross-sectional view of the core member and the mounting unit of the semen collection device shown in FIG. 2, taken along line IV-IV.

As shown in FIG. 4, the wireless charging module 24 can include a transmitting terminal 242 and a receiving terminal 244. The transmitting terminal 242 can be positioned in the base 50. The receiving terminal 244 can be positioned in the receiving chamber 2120 of the main portion 21 of the main body 20 corresponding to the transmitting terminal 242. The base 50 can further include an interface 56, such as USB, in connection with the transmitting terminal 42 and an external power source for providing electronic power to the transmitting terminal 42.

The control circuit 22 also can transmit the signals of the variation of amplitude and frequency of a position of the core member 10 to a portable handheld terminal 200 (see FIG. 6) or internet via the wireless communication module 29. On the contrary, the vibratory element 27 can be controlled by the portable handheld terminal via the wireless communication module 29. In other words, the operator can control the portable handheld terminal 200 to dominate the vibration modes of the vibratory element 27 via the wireless communication module 29.

Figure 6:
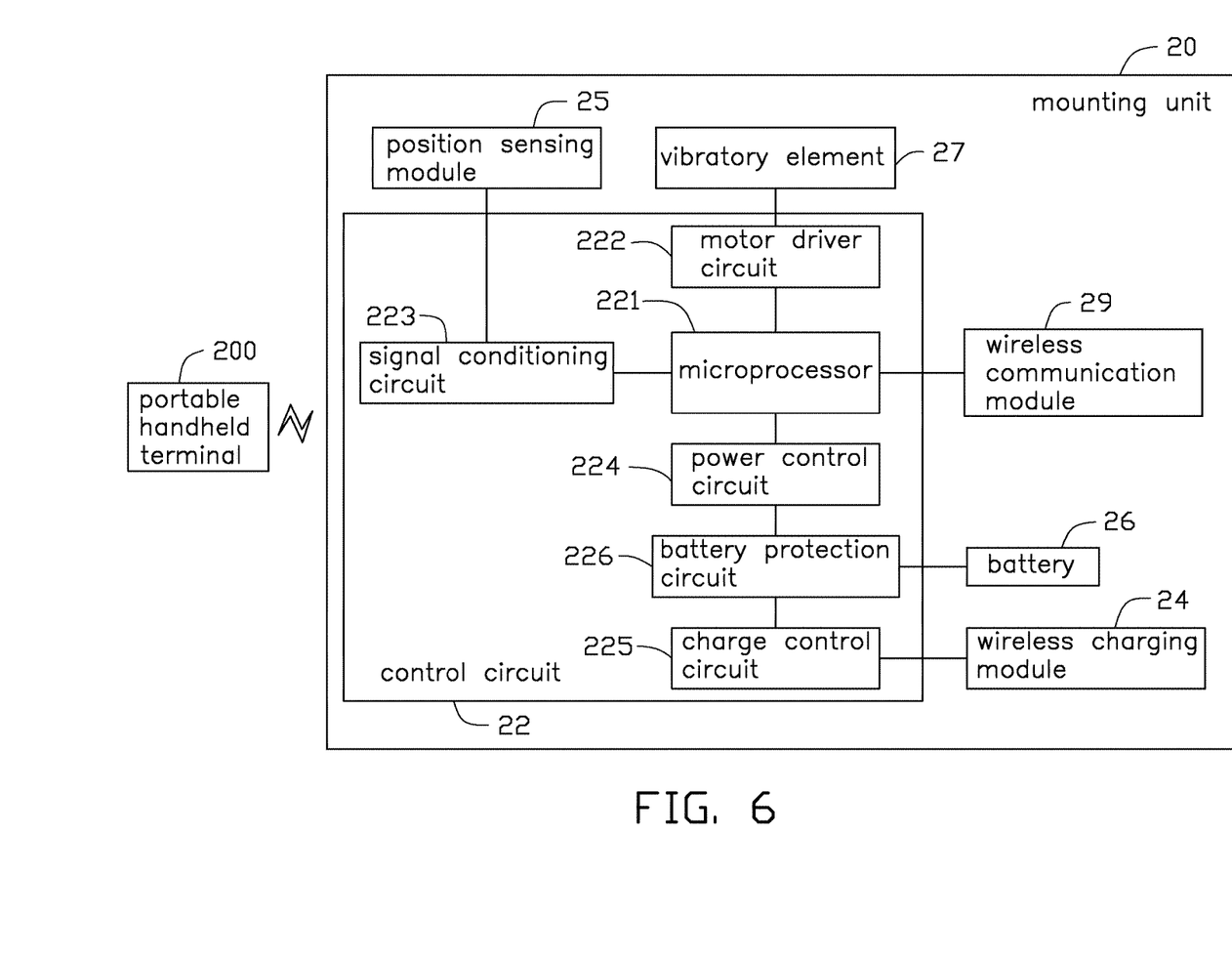
FIG. 6 is a block diagram of the main body of the semen collection device shown in FIG. 1 with an external portable handheld terminal.

FIG. 6 shows a block diagram of the main portion 212 of the main body 21 of the semen collection device 100 with a portable handheld terminal. The control circuit 22 can include a microprocessor 221, a motor driver circuit 222, a signal conditioning circuit 223, a power control circuit 224, a charge control circuit 225, and a battery protection circuit 226. The microprocessor 221 may be substituted in some embodiments with a microcontroller, ASIC, FPGA, SoC, or other processor or electronic device capable of processing instructions and/or signals. In the embodiment, the microprocessor 221 receives input from the position sensing module, maintains mode status information (e.g., state machine information) and controls the system outputs, including directions to motor driver circuit 222 for controlling the vibratory element 27. In the illustrated embodiment, the microprocessor 221 may communicate with a computer, a portable handheld terminal 200, or other electronic devices via the wireless communication module 29.

The motor driver circuit 222 can be in connection with the microprocessor 221. The motor driver circuit 222 converts signals from the microprocessor 221 into signals sufficient to operate the vibratory element 27 according to commands from the microprocessor 221. The signal conditioning circuit 223 can be in connection with the microprocessor 221 for connecting with the position sensing module 25. The power control circuit 24 can be in connection with the microprocessor 221 for controlling the power consumption during various modes of operation of the device. The power control circuit 24 may respond to input from the microprocessor 221 without regard to operator input through the pressing contact module 90. The charge control circuit 28 and battery protection circuit 26 that interface with the wireless charging module 24 to manage the use of the battery 26. The charge control circuit 28 and/or battery protection circuit 26 may be used to control the charging of the battery 26 and the discharging of the battery 26. The charge control circuit 28 and battery protection circuit 26 can be adapted to operate independently from the microprocessor 221.

Figure 7:
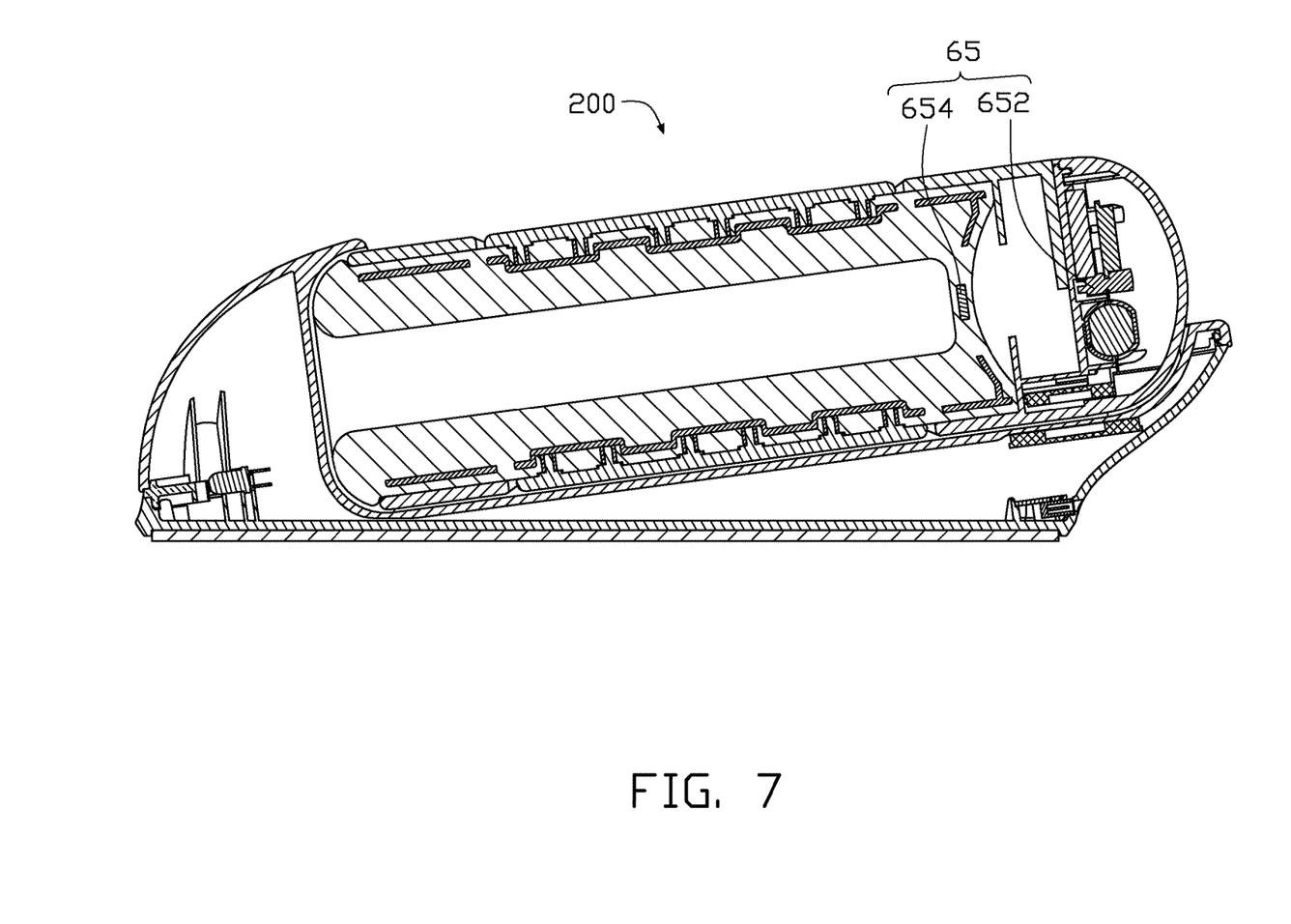
FIG. 7 is a cross-sectional view of a second embodiment of a semen collection device.

FIG. 7 shows a second embodiment of a semen collection device 200, the semen collection device 200 is similar to the semen collection device 100 of the first embodiment, except that a position sensing module 65 of the semen collection device 200 is different from the position sensing module 25 of the semen collection device 100. The position sensing module 65 includes a magnetic member 654 embedded in the flexible base 110 of the flexible body 10, and a Holzer component 652 positioned in the main portion 212 corresponding to the magnetic member 654. The Holzer component 652 can send a change of the distances relative to the corresponding magnetic members 654 when the core member 10 is compressed or stretched.

The embodiments shown and described above are only examples. Many details are often found in the art. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A semen collection device comprising:
   a core member being a cylindrical structure defining an insertion space having an inlet at an end, wherein the core member comprises a flexible body and a built-in piece, the flexible body having a flexible base and an annular sidewall extending from the flexible base to form the cylindrical structure, the built-in piece disposed within the sidewall of the flexible body, the built-in piece being made of a material harder than the flexible body, and the flexible body defining the insertion space having the inlet at the end of the flexible body;
   a mounting unit comprising:
      a main body having a main portion and a receiving portion extending from an end of the main portion,
      a cover hingedly coupled to the receiving portion along an axial direction of the receiving portion at a side of the main portion, the cover and the receiving portion cooperatively defining a cylindrical chamber for fixedly receiving the core member and an opening communicating with the cylindrical chamber for exposing the end of core member having the inlet, and
      a position sensing module located in the main portion substantially close to the opening and configured to detect a variation of amplitude and frequency of a position of the core member.

2. The semen collection device of claim 1, wherein the flexible body further defines a deformable surface at an outer surface of the flexible base facing the main portion of the mounting unit.

3. The semen collection device of claim 1, wherein the built-in piece is a tubular structure disposed in the annular sidewall of the flexible body and surrounding the insertion space.

4. The semen collection device of claim 2, wherein the position sensing module comprises an infrared ray sensor positioned in the main portion toward the opening, and a light reflecting layer formed at the deformable surface of the flexible base of the flexible body corresponding to the infrared ray sensor.

5. The semen collection device of claim 2, wherein the position sensing module comprises a magnetic member embedded in the flexible base of the flexible body, and a Holzer component positioned in the main portion corresponding to the magnetic member.

6. The semen collection device of claim 1, wherein the main body of the mounting unit defines a substantially circular mounting surface; the receiving portion comprises a first semi-cylindrical sidewall extending from an edge of the circular mounting surface; the cover comprises a second semi-cylindrical sidewall hinged with the first semi-cylindrical sidewall, the mounting surface and the first and second semi-cylindrical sidewalls cooperatively define the cylindrical chamber for fixedly receiving the core member.

7. The semen collection device of claim 6, wherein the receiving portion further comprises a pair of first end side surfaces extending along the axial direction of the receiving portion substantially perpendicular to the circular mounting surface; the cover further comprises a pair of second end side surfaces extending along the axial direction of the receiving portion substantially perpendicular to the circular mounting surface; one of the second end side surfaces of the cover is hinged with one of the first end side surfaces with a hinge.

8. The semen collection device of claim 7, wherein the other of the first end side surfaces defines a first depression for fixing a first magnetic member, and the other of the second end side surface defines a second depression for fixing a second magnetic member according to the first magnetic member; the cover is configured to rotate relative to the receiving portion until the second magnetic member is fixed on the first magnetic member, thereby the cover being closed on the receiving portion.

9. The semen collection device of claim 6, wherein the first semi-cylindrical sidewall further defines a first through hole therein; the second semi-cylindrical sidewall further defines a second through hole therein.

10. The semen collection device of claim 1, wherein the main portion of the main body defines a receiving chamber; the main portion further comprises a control circuit, a wireless communication module, a wireless charging module, a battery, and a vibratory element; the control circuit, the wireless communication module, the wireless charging module, the battery, and the vibratory element received in the receiving chamber; the wireless communication module, the wireless charging module, the battery, the vibratory element electrically coupled to the control circuit respectively.

11. The semen collection device of claim 10, wherein the wireless communication module is configured to receive a control signal, and transmit the control signal to the control circuit for controlling vibrations of the vibratory element.

12. The semen collection device of claim 10, wherein the control circuit comprises a microprocessor receiving input from the position sensing module.

13. The semen collection device of claim 12, wherein the control circuit further comprises a motor driver circuit for converting signals from the microprocessor into signals sufficient to operate the vibratory element according to commands from the microprocessor.

14. The semen collection device of claim 12, wherein the control circuit further comprises a signal conditioning circuit in connection with the microprocessor for connecting with the position sensing module.

15. The semen collection device of claim 12, wherein the control circuit further comprises a power control circuit in connection with the microprocessor for controlling the power consumption during various modes of operation of the device.

16. The semen collection device of claim 12, wherein the control circuit further comprises a charge control circuit configured for controlling the charging of the battery and the discharging of the battery.

* * * * *